(12) United States Patent
Zhang

(10) Patent No.: US 10,024,260 B2
(45) Date of Patent: Jul. 17, 2018

(54) SYSTEM FOR SENSING PARTICULATE MATTER

(71) Applicant: Ford Global Technologies, LLC, Dearborn, MI (US)

(72) Inventor: Xiaogang Zhang, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 107 days.

(21) Appl. No.: 15/168,528

(22) Filed: May 31, 2016

(65) Prior Publication Data

US 2017/0342923 A1 Nov. 30, 2017

(51) Int. Cl.
| | |
|---|---|
| *F01N 3/00* | (2006.01) |
| *F01N 3/02* | (2006.01) |
| *F02D 41/02* | (2006.01) |
| *F01N 3/027* | (2006.01) |
| *F01N 9/00* | (2006.01) |
| *F01N 13/00* | (2010.01) |
| *F02D 41/14* | (2006.01) |
| *G01N 15/06* | (2006.01) |
| *F02D 41/00* | (2006.01) |
| *F02D 41/22* | (2006.01) |
| *G01N 15/00* | (2006.01) |

(52) U.S. Cl.
CPC ......... *F02D 41/029* (2013.01); *F01N 3/0275* (2013.01); *F01N 9/002* (2013.01); *F01N 13/008* (2013.01); *F02D 41/1466* (2013.01); *F02D 41/1494* (2013.01); *G01N 15/0606* (2013.01); *G01N 15/0656* (2013.01); *F01N 2560/05* (2013.01); *F02D 41/0047* (2013.01); *F02D 2041/228* (2013.01); *F02D 2250/26* (2013.01); *G01N 2015/0046* (2013.01)

(58) Field of Classification Search
CPC .. F01N 13/008; F01N 2560/05; F01N 3/0275; F01N 9/002; F02D 2041/228; F02D 2250/26; F02D 41/0047; F02D 41/029; F02D 41/1466; F02D 41/1494; G01N 15/06
USPC ................................. 60/276, 277, 297, 311
See application file for complete search history.

(56) References Cited

U.S. PATENT DOCUMENTS

| | | | |
|---|---|---|---|
| 7,810,375 B2 | 10/2010 | Weyl et al. | |
| 8,656,763 B2 * | 2/2014 | Yoshioka | ................ F01N 3/023 73/114.31 |
| 9,803,524 B2 * | 10/2017 | Kubinski | ................ F01N 3/027 |
| 9,804,074 B2 * | 10/2017 | Weber | ................ G01N 15/0656 |
| 9,863,301 B2 * | 1/2018 | Yoshidome | ............. F01N 11/00 |
| 2015/0077350 A1 | 3/2015 | Hinson | |
| 2015/0355066 A1 | 12/2015 | Zhang | |
| 2015/0355067 A1 | 12/2015 | Zhang et al. | |
| 2016/0131013 A1 | 5/2016 | Yi et al. | |

OTHER PUBLICATIONS

Zhang, Xiaogang, "Method and System for Exhaust Particulate Matter Sensing," U.S. Appl. No. 15/063,703, filed Mar. 8, 2016, 61 pages.

* cited by examiner

*Primary Examiner* — Phutthiwat Wongwian
*Assistant Examiner* — Diem Tran
(74) *Attorney, Agent, or Firm* — Julia Voutyras; McCoy Russell LLP

(57) ABSTRACT

Methods and systems are provided for a particulate matter sensor. In one example, the sensor may include a concave inlet for admitting exhaust gas from an exhaust passage downstream of a particulate filter into the sensor.

6 Claims, 6 Drawing Sheets

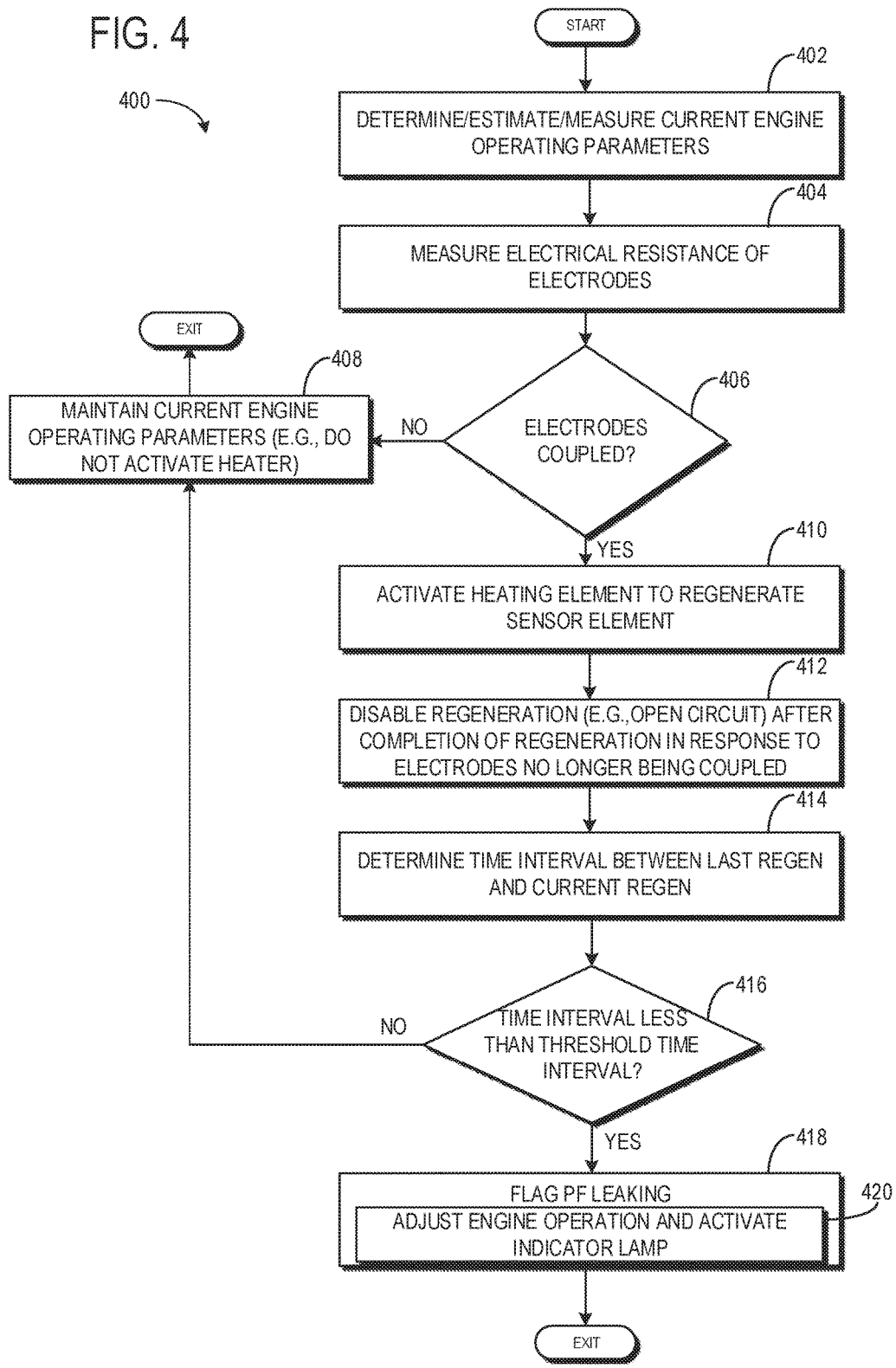

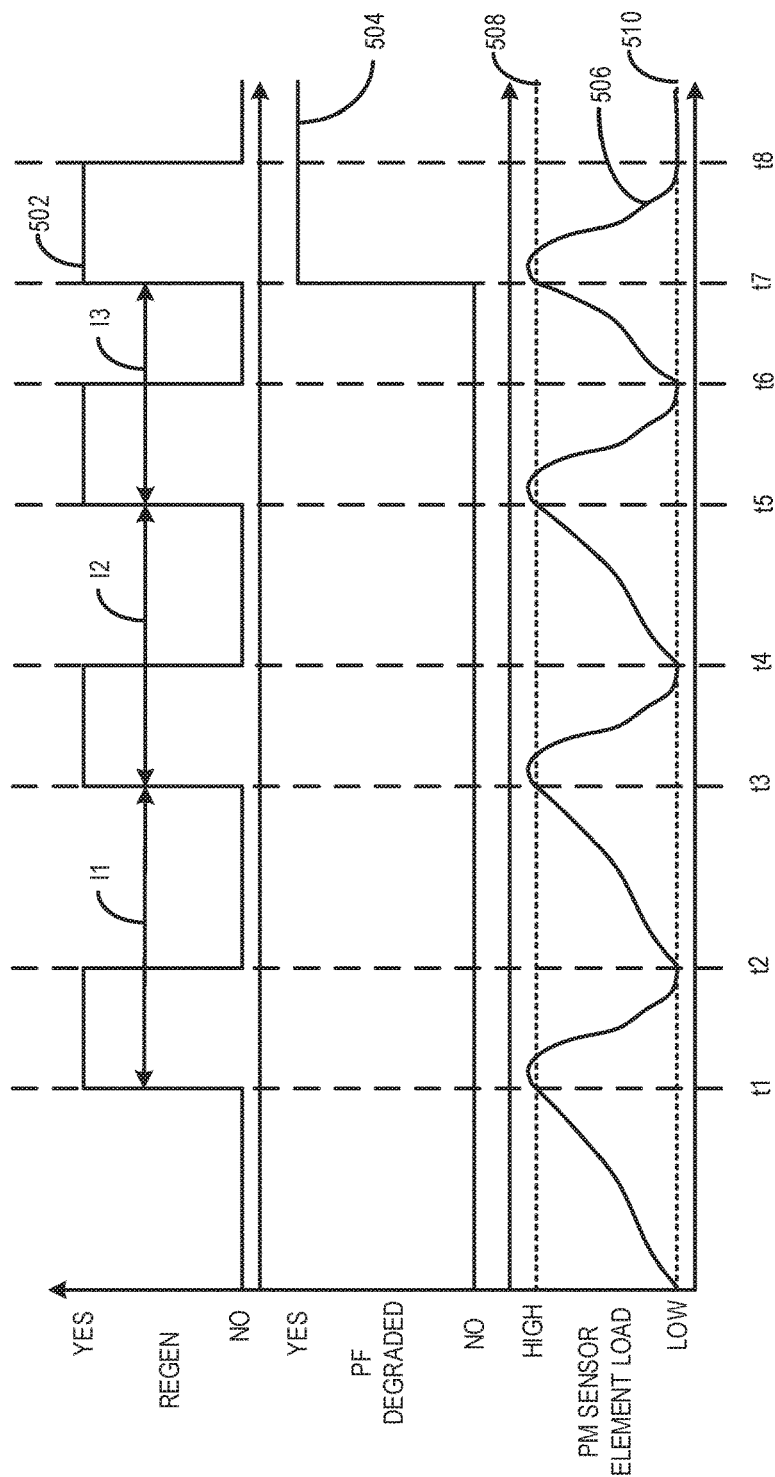

SYSTEM FOR SENSING PARTICULATE MATTER

FIELD

The present application relates to sensing particulate matter in an exhaust system.

BACKGROUND/SUMMARY

Particulate matter filters are increasingly used in automotive emissions systems for reducing particulate concentrations in engine exhaust. When soot accumulates to a threshold level on the particulate filter, a filter regeneration process may be used to burn off the accumulated soot under controlled engine operating conditions. However, over time, such particulates filters can suffer irreversible decreases in trapping efficiencies as the filter develops cracks due to uncontrolled temperature excursion during the filter regeneration process. Losses in trapping efficiency of the particulate filter may result in increased particulate matter emissions well above the regulated limit.

Increasingly stringent particulate matter emissions standards and proposed government-mandated on-board diagnostic (OBD) requirements for monitoring the trapping efficiency of a particulate filter have stimulated much research into new techniques for monitoring particulate filter performance. One method includes determining a differential pressure across a particulate filter. If the differential pressure is less than a threshold differential pressure, then the particulate filter may be leaking. However, this method may not be suitable for detecting a failure of the filter due to interference effects from ash loading in the filter. Other methods to determine particulate filter leakage include utilizing a soot sensor, located downstream of a particulate filter, to monitor a soot load in exhaust flow and signaling when the soot load exceeds a soot threshold (e.g., the soot threshold may be based on a threshold amount of acceptable soot leakage based on particulate matter emissions).

However, the inventors herein have recognized potential issues with such systems. As one example, the soot sensor may have low sensitivity to leaked soot due to a relatively small portion of soot being deposited on the soot sensor. This may be due to an exhaust pipe geometry and/or poor mixing of the exhaust gas. Furthermore, large diesel particulates and/or water droplets may impinge onto surfaces of the soot sensor, altering the soot sensor reading.

In one example, the issues described above may be addressed by a system for a particulate matter sensor disposed along an exhaust passage comprising an outer tube coaxial with an inner tube having a concave bottom with a central opening, and where perforations of the inner tube face a curved sensor element located in an annular space between the outer tube and the inner tube. In this way, exhaust gas may flow through the perforations to the sensor element to accurately determine a condition of a particulate filter upstream of the particulate matter sensor in the exhaust passage.

As one example, the perforations face a first surface of the sensor element comprising a pair of interdigitated electrodes spaced apart from one another. There may be a heating element coupled to a second surface of the sensor substrate facing an interior wall of the outer tube. The sensor substrate is configured to capture soot where the soot may be deposited between the pair of interdigitated electrodes. As the soot accumulates, the separated electrodes may become bridged (e.g., electrically coupled), decreasing an electrical resistance of one of the two electrodes. In response to the electrical resistance being decreased, the heating element may be activated to burn off accumulated soot on the sensor substrate. Additionally, a particulate filter in the exhaust passage upstream of the particulate matter sensor may be regenerated in response to the electrodes becoming bridged. A time interval between subsequent regenerations of the sensor substrate may be measured, where a degradation of the particulate filter may be determined based on the time interval being less than a threshold time interval.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIGS. 2-3D are shown approximately to scale, however, other dimensions may be used.
FIG. 4 shows a method for determining degradation of a particulate filter in the exhaust pipe.
FIG. 5 shows an operating sequence for monitoring a time interval between regenerations of a PM sensor assembly.

DETAILED DESCRIPTION

Figure 1:
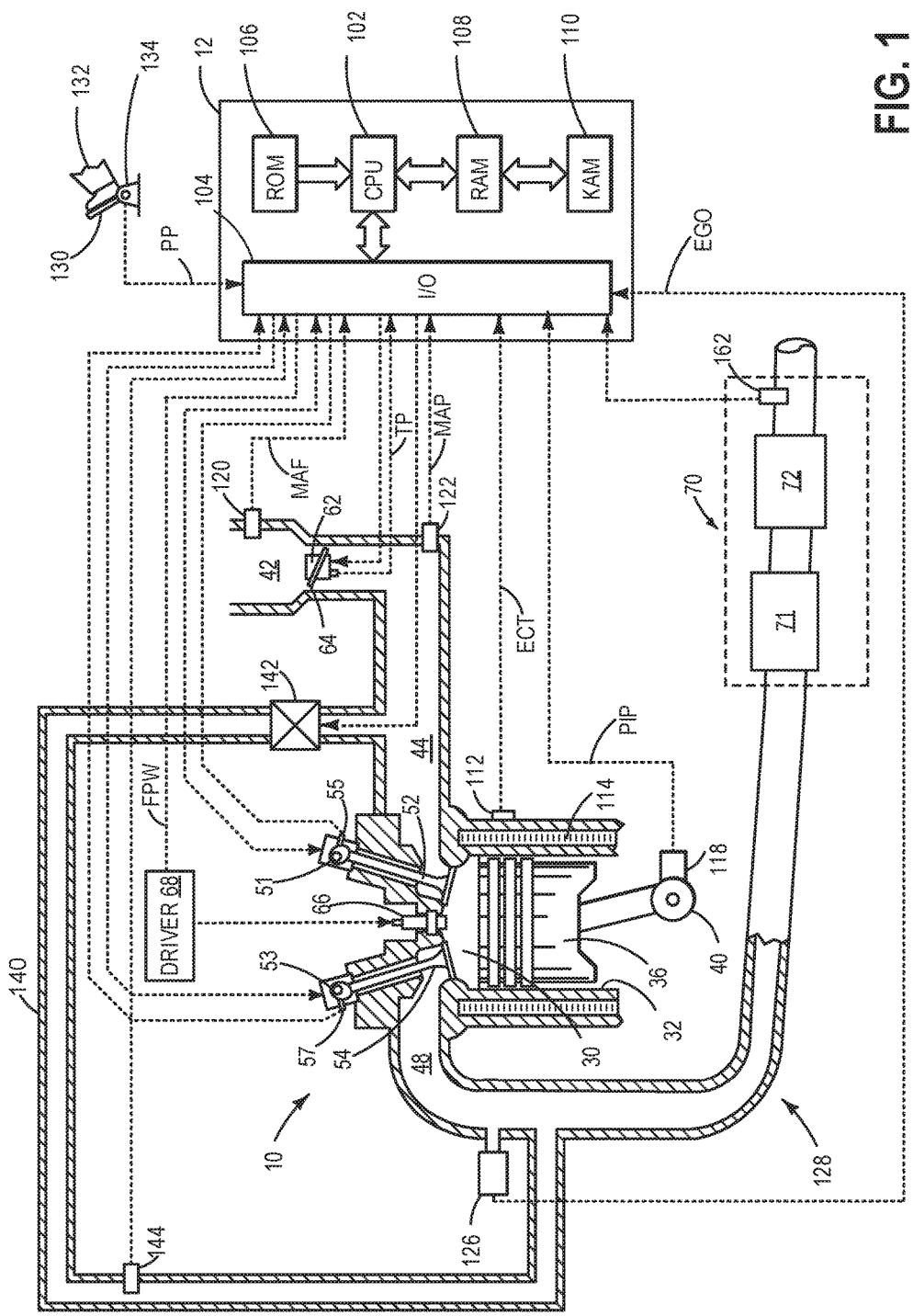
FIG. 1 is a schematic diagram of an engine.
Figure 2:
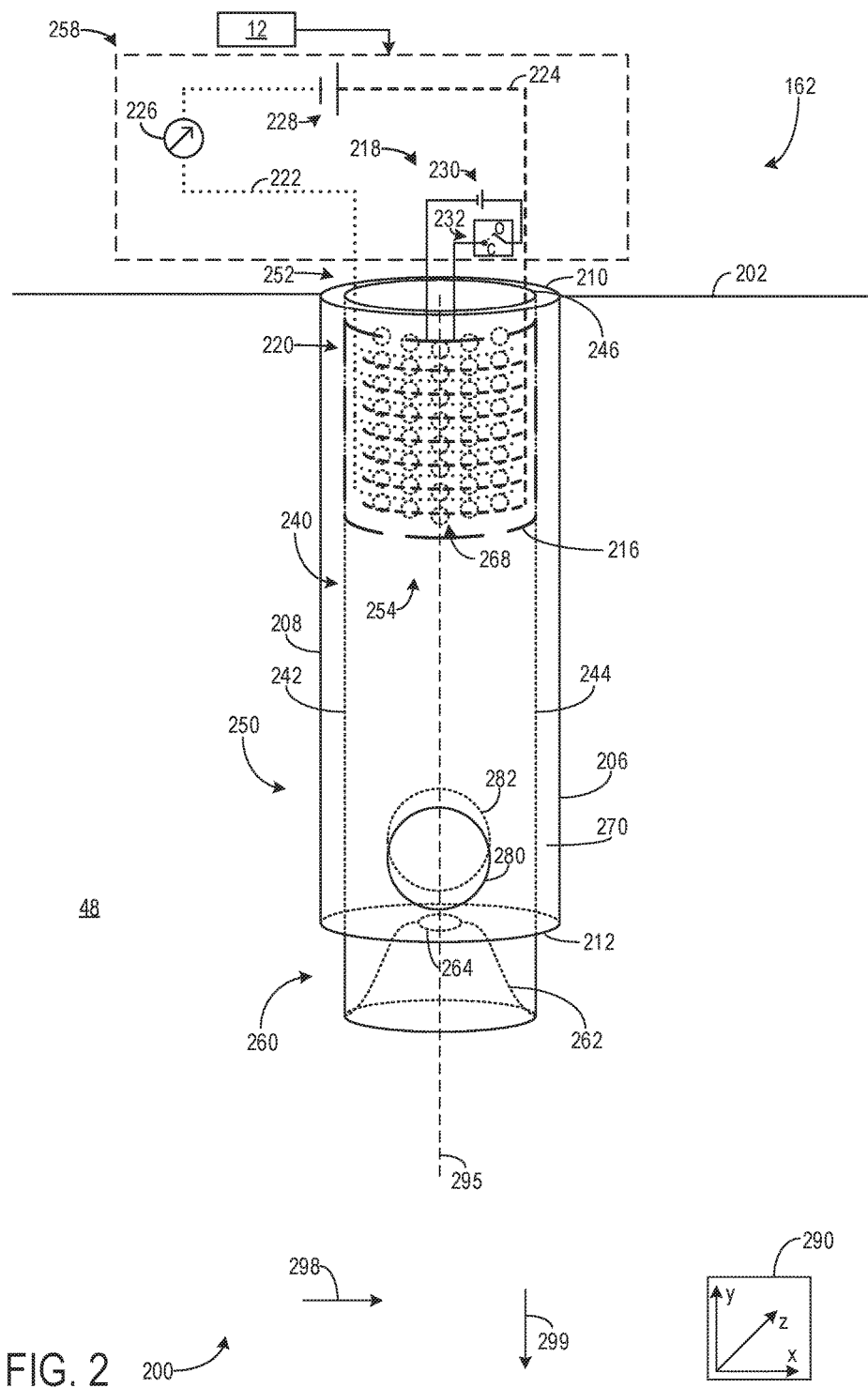
FIG. 2 shows a schematic illustration of a particulate matter (PM) sensor assembly.
Figure 3A:
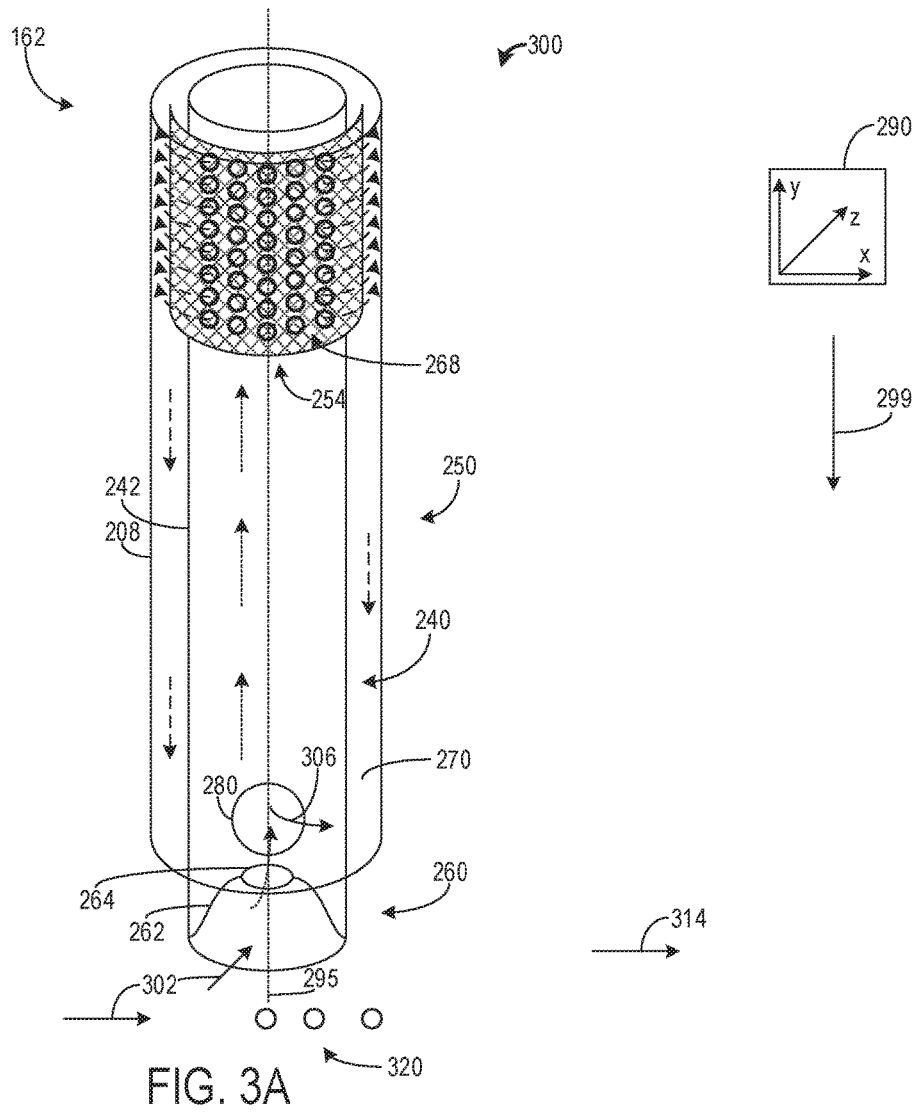
FIGS. 3A and 3B show cross-sectional views of components of the PM sensor assembly.
Figure 3B:
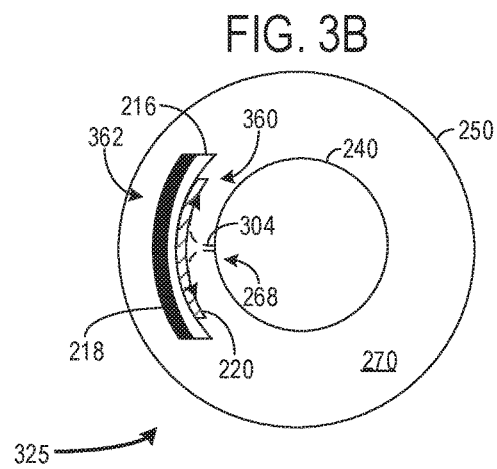

The following description relates to sensing particulate matter (PM) in an exhaust flow of an engine system, such as an engine system shown in FIG. 1. A PM sensor placed in an exhaust passage of the engine system may include a first outer tube and a second inner tube. A PM sensor element may be enclosed between the second inner tube and first outer tube as shown in FIG. 2. Perforations of the second inner tube correspond with a location of the PM sensor element such that exhaust gas received by the second inner tube through a concave projection flows out the perforations directly toward the PM sensor element. Electrodes of the PM sensor element face the perforations and may become bridged as soot from the exhaust gas is deposited onto a sensor substrate of the PM sensor element. Cross-sections of the first outer tube, the second inner tube, and the PM sensor element are shown in FIGS. 3A and 3B, respectively. Surfaces of the sensor substrate of the PM sensor element are depicted in greater detail in FIGS. 3C and 3D. A method for determining a condition of a particulate filter (PF) in the exhaust passage based on a regeneration of the PM sensor element is shown in FIG. 4. Furthermore, the method includes determining a degradation of the PF in the exhaust passage based on a time interval between regenerations of the PM sensor element. The PF may develop cracks as a number of PF regenerations increases. As a result, a greater amount of particulate matter may flow through the cracked PF to the PM sensor element, thereby causing the PM sensor element regeneration time intervals to decrease. Changes in the PM sensor element time interval are graphically displayed in FIG. 5.

FIGS. 1-3D show example configurations with relative positioning of the various components. If shown directly contacting each other, or directly coupled, then such elements may be referred to as directly contacting or directly coupled, respectively, at least in one example. Elements described as directly downstream or directly upstream of one another may be defined herein such that there are no intervening components between the two comparative elements. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Referring now to FIG. 1, it shows a schematic diagram with one cylinder of multi-cylinder engine 10, which may be included in a propulsion system of a vehicle. Engine 10 may be controlled at least partially by a control system including a controller 12 and by input from a vehicle operator 132 via an input device 130. In this example, input device 130 includes an accelerator pedal and a pedal position sensor 134 for generating a proportional pedal position signal PP. A combustion chamber 30 (also termed, cylinder 30) of the engine 10 may include combustion chamber walls 32 with a piston 36 positioned therein. Piston 36 may be coupled to a crankshaft 40 so that reciprocating motion of the piston is translated into rotational motion of the crankshaft. Crankshaft 40 may be coupled to at least one drive wheel (not shown) of a vehicle via an intermediate transmission system (not shown). Further, a starter motor (not shown) may be coupled to the crankshaft 40 via a flywheel (not shown) to enable a starting operation of the engine 10.

Combustion chamber 30 may receive intake air from an intake manifold 44 via an intake passage 42 and may exhaust combustion gases via an exhaust passage 48. The intake manifold 44 and the exhaust passage 48 can selectively communicate with the combustion chamber 30 via intake valve 52 and exhaust valve 54 respectively. In some embodiments, the combustion chamber 30 may include two or more intake valves and/or two or more exhaust valves.

In the example depicted in FIG. 1, the intake valve 52 and exhaust valve 54 may be controlled by cam actuation via respective cam actuation systems 51 and 53. The cam actuation systems 51 and 53 may each include one or more cams and may utilize one or more of cam profile switching (CPS), variable cam timing (VCT), variable valve timing (VVT), and/or variable valve lift (VVL) systems that may be operated by the controller 12 to vary valve operation. The position of the intake valve 52 and the exhaust valve 54 may be determined by position sensors 55 and 57, respectively. In alternative embodiments, the intake valve 52 and/or exhaust valve 54 may be controlled by electric valve actuation. For example, the cylinder 30 may alternatively include an intake valve controlled via electric valve actuation and an exhaust valve controlled via cam actuation including CPS and/or VCT systems.

In some embodiments, each cylinder of the engine 10 may be configured with one or more fuel injectors for providing fuel thereto. As a non-limiting example, the cylinder 30 is shown including one fuel injector 66. Fuel injector 66 is shown coupled to the cylinder 30 for injecting fuel directly therein in proportion to the pulse width of signal FPW received from controller 12 via electronic driver 68. In this manner, fuel injector 66 provides what is known as direct injection of fuel into combustion chamber 30. It will also be appreciated that the cylinder 30 may receive fuel from a plurality of injections during a combustion cycle. In other examples, the fuel injector may be mounted in the side of the combustion chamber or in the top of the combustion chamber, for example. Fuel may be delivered to fuel injector 66 by a fuel system (not shown) including a fuel tank, a fuel pump, and a fuel rail.

In the example shown in FIG. 1, engine 10 is configured as a diesel engine that combusts air and diesel fuel through compression ignition. In other embodiments, the engine 10 may combust a different fuel including gasoline, biodiesel, or an alcohol containing fuel blend (e.g., gasoline and ethanol, or gasoline and methanol) through compression ignition and/or spark ignition. Thus, the embodiments described herein may be used in any suitable engine, including but not limited to, diesel and gasoline compression ignition engines, spark ignition engines, direct or port injection engines, etc.

The intake passage 42 may include a throttle 62 having a throttle plate 64. In this particular example, the position of the throttle plate 64 may be varied by controller 12 via a signal provided to an electric motor or actuator included with the throttle 62, a configuration that is commonly referred to as electronic throttle control (ETC). In this manner, the throttle 62 may be operated to vary the intake air provided to the combustion chamber 30 among other engine cylinders. The position of the throttle plate 64 may be provided to the controller 12 by throttle position signal TP. The intake passage 42 may include a mass air flow sensor 120 and a manifold air pressure sensor 122 for providing respective signals MAF and MAP to the controller 12.

Further, in the disclosed embodiments, an exhaust gas recirculation (EGR) system may route a desired portion of exhaust gas from the exhaust passage 48 to the intake manifold 44 via an EGR passage 140. The amount of EGR provided may be varied by controller 12 via an EGR valve 142. By introducing exhaust gas to the engine 10, the amount of available oxygen for combustion is decreased, thereby reducing combustion flame temperatures and reducing the formation of NOx, for example. As depicted, the EGR system further includes an EGR sensor 144 which may be arranged within the EGR passage 140 and may provide an indication of one or more of pressure, temperature, and concentration of the exhaust gas. Under some conditions, the EGR system may be used to regulate the temperature of the air and fuel mixture within the combustion chamber, thus providing a method of controlling the timing of ignition during some combustion modes. Further, during some conditions, a portion of combustion gases may be retained or trapped in the combustion chamber by controlling exhaust valve timing, such as by controlling a variable valve timing mechanism.

An exhaust system 128 includes an exhaust gas sensor 126 coupled to the exhaust passage 48 upstream of an emission control system 70. Exhaust gas sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), NOx, HC, or CO sensor.

Emission control system 70 is shown arranged along exhaust passage 48 downstream of exhaust gas sensor 126. Emission control system 70 may be a selective catalytic reduction (SCR) system, three way catalyst (TWC), NOx trap, various other emission control devices, or combinations thereof. For example, emission control system 70 may include an SCR catalyst 71 and a particulate filter (PF) 72. In some embodiments, PF 72 may be located downstream of the SCR catalyst 71 (as shown in FIG. 1), while in other embodiments, PF 72 may be positioned upstream of the SCR catalyst 71 (not shown in FIG. 1). Emission control system 70 may further include exhaust gas sensor 162. Sensor 162 may be any suitable sensor for providing an indication of a concentration of exhaust gas constituents such as a NOx, NH3, EGO, or particulate matter (PM) sensor, for example. In some embodiments sensor 162 may be located downstream of PF 72 (as shown in FIG. 1), while in other embodiments, sensor 162 may be positioned upstream of PF 72 (not shown in FIG. 1). Further, it will be appreciated that more than one sensor 162 may be provided in any suitable position.

As described in more detail with reference to FIG. 2, sensor 162 may be a PM sensor and may measure the mass or concentration of particulate matter and/or soot downstream of PF 72. For example, sensor 162 may be a soot sensor. Sensor 162 may be operatively coupled to controller 12 and may communicate with controller 12 to indicate a concentration of particulate matter within exhaust exiting PF 72 and flowing through exhaust passage 48. In this way, sensor 162 may detect leakages from PF 72. In the description herein, particulate matter and soot may be used interchangeably.

Further, in some embodiments, during operation of engine 10, emission control system 70 may be periodically reset by operating at least one cylinder of the engine within a particular air/fuel ratio.

Controller 12 is shown in FIG. 1 as a microcomputer, including a microprocessor unit 102, input/output ports 104, an electronic storage medium for executable programs and calibration values shown as a read only memory chip 106 in this particular example, random access memory 108, keep alive memory 110, and a data bus. The controller 12 may be in communication with and, therefore, receive various signals from sensors coupled to the engine 10, in addition to those signals previously discussed, including measurement of inducted mass air flow (MAF) from the mass air flow sensor 120; engine coolant temperature (ECT) from a temperature sensor 112 coupled to a cooling sleeve 114; a profile ignition pickup signal (PIP) from a Hall effect sensor 118 (or other type) coupled to the crankshaft 40; throttle position (TP) from a throttle position sensor; absolute manifold pressure signal, MAP, from the sensor 122; and exhaust constituent concentration from the exhaust gas sensor 126. Engine speed signal, RPM, may be generated by controller 12 from signal PIP.

As described above, FIG. 1 shows only one cylinder of a multi-cylinder engine, and each cylinder may similarly include its own set of intake/exhaust valves, fuel injector, spark plug, etc.

FIG. 2 shows an exterior side perspective view 200 of the exhaust gas sensor 162. As such, components previously introduced are numbered similarly in subsequent figures. In one example, the exhaust gas sensor 162 is a particulate matter (PM) sensor, as will be described below. A PM sensor element 254 and its components are depicted in lines bolder than other portions of the PM sensor 162 depicted in FIG. 2. Bolder lines are thicker than thinner lines. Portions of the PM sensor 162 in dashed line are behind portions of the PM sensor 162 indicated in solid line.

An axis system 290 is shown comprising three axes, namely, an x-axis parallel to the horizontal direction, a y-axis parallel to the vertical direction, and a z-axis perpendicular to the x- and y-axes. The axis system 290 may be used to describe the relative positioning of components of the PM sensor 162. A "height" of the PM sensor 162 and/or its components may be used to define the extent of the components along the y-axis. Similarly, a "length" of components of the PM sensor 162 may be used to refer to the physical extent of the components along the x-axis. The physical extent of components along the z-axis may be referred to as a "width."

The PM sensor element 254 includes a pair of planar interdigitated electrodes 220 forming a "comb" structure. These electrodes may be typically manufactured from metals such as platinum, gold, osmium, rhodium, iridium, ruthenium, aluminum, titanium, zirconium, and the like, as well as, oxides, cements, alloys and combination comprising at least one of the foregoing metals. The electrodes 220 are formed on a substrate 216 that may be manufactured from highly electrically insulating materials. Possible electrically insulating materials may include oxides such as alumina, zirconia, yttria, lanthanum oxide, silica, and combinations comprising at least one of the foregoing, or any like material capable of inhibiting electrical communication and providing physical protection for the pair of interdigitated electrodes. The spacing between the comb "tines" of the two electrodes may typically be in the range from 10 micrometers to 100 micrometers with the linewidth of each individual "tine" being about the same value, although the latter is not necessary. As shown in FIG. 2, the interdigitated electrodes 220 extend along and cover a portion of the substrate 216.

A positive electrode of the pair of interdigitated electrodes 220 is connected with connecting wires 224 to a positive terminal of a voltage source 228 of an electric circuit 258. A negative electrode of the pair of interdigitated electrodes 220 is connected to a measurement device 226 via a connecting wire 222, and further connected to a negative terminal of the voltage source 228 of the electric circuit 258. The interconnecting wires 222 and 224, the voltage source 228 and the measurement device 226 are part of the electric circuit 258 and are housed outside the exhaust passage 48 (as one example, <1 meter away). Further, the voltage source 228 and the measurement device of the electric circuit 258 may be controlled by a controller, such as controller 12 of FIG. 1, so that particulate matter collected at the PM sensor may be used for diagnosing leaks in a PF upstream of the exhaust gas sensor (e.g., PF 72 in the embodiment of FIG. 1), for example. As such, the measurement device 226 may be any device capable of reading a resistance change across the electrodes, such as a voltmeter. As PM or soot particles get deposited between the electrodes 220, the resistance between the electrode pair may start to decrease, which is indicated by an increase in the current measured by the measurement device 226 for a fixed voltage (usually 45 V) electric source 228. The controller 12 may be able to determine the resistance between the electrodes 220 as a function of electric current measured by the measurement device 226 and infer a corresponding PM or soot load on the planar electrodes 220 of the PM sensor 162. By monitoring the load on the PM sensor 162, the exhaust soot load downstream of the DPF may be determined, and thereby used to diagnose and monitor the health and functioning of the DPF.

The PM sensor element 254 also includes a heating element 218 that is be integrated into the sensor substrate 216. In alternate embodiments, the PM sensor element 254 may not include a heating element 218. The heating element 218 may comprise, but is not limited to, a temperature sensor, and a heater. Possible materials for the heater and the temperature sensor forming the heating element 218 may include platinum, gold, palladium, and the like; and alloys, oxides, and combinations comprising at least one of the foregoing materials, with platinum/alumina, platinum/palladium, platinum, and palladium. The heating element 218 may be used for regenerating the PM sensor element 254. Specifically, during conditions when the particulate matter load or soot load of the PM sensor element 254 is higher than a threshold, heating element 218 may be operated to burn accumulated soot particles from the surface of sensor. During PM sensor regeneration, the controller 12 may provide a voltage to a voltage source 230, which is needed for operating the heating element 218. In addition, the controller may close the switch 232 for a threshold time to apply the voltage via the voltage source 230 to the heating element 218 in order to raise the temperature of the heating element 218. Subsequently, when the sensor electrodes are sufficiently clean, the controller may open the switch 232 to stop heating the heating element 218. By intermittently regenerating the PM sensor 162, it may be returned to a condition (e.g., unloaded or only partially loaded condition) more suitable for collecting exhaust soot. In addition, accurate information pertaining to the exhaust soot level may be inferred from the sensor regeneration and this information may be used by the controller for diagnosing leaks in the particulate filter. The sensitivity of the PM sensor may be affected by large particulates and/or water droplets getting deposited on the PM sensor element 254. The first outer tube 250 and the second inner tube 240 may be configured to limit or prevent a flow of large particulates and/or water droplets.

The first outer tube 250 may be a hollow cylindrical tube with an upstream tube wall 208 (e.g., upstream facing wall), a downstream tube wall 206 (e.g., downstream facing wall), a front wall, and a back wall (opposite the front wall). The upstream tube wall 208 may be closer to the PF than any other wall of the first outer tube 250 when positioned in an exhaust passage such as exhaust passage 48 shown in FIG. 1, where the PF is positioned upstream of the PM sensor 162. A top surface 210 of the first outer tube 250 may further include an inset portion 252 through which the PM sensor element 254 and its accompanying electrical connections may be inserted into the PM sensor 162, and further be sealed to protect the PM sensor element 254 housed within the PM sensor 162. The first outer tube 250 may be mounted onto an exhaust pipe 202 of the exhaust passage 48 via one or more sensor bosses or other suitable coupling elements such that the central axis 295 of the first outer tube 250 is perpendicular to the exhaust passage 48 and a direction of the exhaust flow through the exhaust passage (shown by arrow 298). The depth to which the first outer tube 250 extends into the exhaust passage may depend on the exhaust pipe 202 diameter. In some examples, the first outer tube 250 may extend to about one third or two thirds of a diameter of the exhaust pipe 202. A bottom 212 of the first outer tube 250 is parallel to a horizontal direction relative to a direction of gravity shown by arrow 299. The bottom 212 of the first outer tube 250 is closed (e.g., sealed) such that exhaust gas may not flow directly from the exhaust passage 48 to the first outer tube 250. The first outer tube 250 includes a first outlet 280 on the front wall and a second outlet 282 on the back wall. The outlets are located directly across from one another along a common axis and face a direction perpendicular to arrow 298. As such, the front wall and the back wall of the first outer tube 250 may be surfaces of the hollow first outer tube 250 that are different from the upstream wall 208 and the downstream wall 206 due to the outlets being located thereon. While the outlets 280 and 282 are shown as elliptical holes, other shapes and sizes of the outlets 280 and 282 may also be used without departing from the scope of this disclosure. Furthermore, the outlets 280 and 282 may be mismatched and unequal in shape in some examples, while being identical in other examples.

The PM sensor 162 further includes the second inner tube 240 concentric with the first outer tube 250 about the central axis 295. The second inner tube 240 is partially enclosed in the first outer tube 250, with a diameter of the second inner tube 240 being less than a diameter of the first outer tube 250. Therefore, an annular space 270 may be formed between the first outer tube 250 and the second inner tube 240. Specifically, the annular space 270 may be formed between an exterior surface of the second inner tube 240 and an interior surface of the first outer tube 250. In alternate embodiments, the central axis of the first outer tube 250 may not coincide with, but may be parallel to, the central axis of the second inner tube 240. However, an annular space 270 between the first outer tube and the second inner tube may be maintained.

The second inner tube 240 comprises surfaces similar to surfaces of the first outer tube 250. Specifically, the second inner tube 240 comprises an upstream face 242, a downstream face 244, a front face, and a back face, which face directions similar to the upstream wall 208, the downstream wall 206, the front wall, and the back wall of the first outer tube 250, respectively. A top surface 246 of the second inner tube 240 is coplanar with the top 210 of the first outer tube 250, where the top surfaces constitute the inset portion 252. Furthermore, the top surface 246 of the second inner tube 240 is physically coupled to the top 210 of the first outer tube 250 via welds, fusions, adhesives, or other suitable couplings elements. The top 210 and the top surface 246 are hermetically sealed to exhaust pipe 202 such that exhaust gas in the PM sensor 162 may not flow directly out of the first outer tube 250 or the second inner tube 240, through the exhaust pipe 202, and to the engine and/or an ambient atmosphere. The second inner tube 240 further comprises a plurality of perforations 268 directed toward the interdigitated electrodes 220 coupled to the sensor substrate 216. Perforations 268 may be substantially identical and spaced away from each other equidistantly. In one example, there are 40 perforations 268 separated into eight rows and five columns. In alternate examples, the perforations 268 may be spaced and arranged differently while still being directed at the sensor substrate 216. Thus, the sensor substrate 216 may be located in the annular space 270 between the first outer tube 250 and the second inner tube 240. In one example, the sensor substrate 216 is curved, where the curvature of the sensor substrate 216 is similar to a curvature of the first outer tube 250 and the second inner tube 240. In other examples, the curvature of the sensor substrate 216 may be more extreme than a curvature of one or more of the first outer tube 250 and the second inner tube 240. Alternatively, the sensor substrate 216 may be planar (e.g., not curved) without departing from the scope of the present disclosure.

The sensor substrate 216 traverses a portion of the circumference of the second inner tube 240. An arc length of the sensor substrate 216 may be less than half of a circumference of the second inner tube 240. In one example, the arc length of the sensor substrate 216 is between 50 to 80% of half of the circumference of the second inner tube 240. Exhaust gas from the perforations 268 may flow directly to the sensor substrate 216. As such, the perforations 268 may extend around a portion of the circumference of the second inner tube 240 less than or equal to the arc length of the sensor substrate 216.

A bottom portion 260 of the second inner tube 240 extends below and outside of the first outer tube 250 into the exhaust passage 48. In one example, the bottom portion 260 of the second inner tube 240 may be defined as a portion of the second inner tube 240 located below a sealed coupling between the bottom 212 of the first outer tube 250 and exterior surfaces of the second inner tube 240. In this way, the bottom portion 260 of the second inner tube 240 may be the only portion of the second inner tube 240 directly exposed to exhaust gas in the exhaust passage 48. The bottom portion 260 comprises a concave projection 262 protruding into an interior of the second inner tube 240. The projection 262 is bell-shaped, decreasing in diameter from its base to an opening and/or inlet 264 configured to admit exhaust gas into the second inner tube 240. It will be appreciated that the projection may be other shapes suitable for admitting exhaust as into the second inner tube 240 while limited the flow of large particulates and/or water droplets into the second inner tube. Specifically, the projection may be spherical, pyramidal, dome-shaped, or other shapes without departing from the scope of the present disclosure. In one example, the opening 264 is co-planar with a plane of the bottom 212 of the first outer tube 250. In alternate embodiments, the opening 264 may be vertically higher or lower than the bottom 212 of the first outer tube 250.

The projection 262 may inhibit the flow of large particulates and/or water droplets from flowing into the second inner tube 240 due to its shape (e.g., concavity and/or curvature). The momentum of the large particulates and/or water droplets is greater than the momentum of smaller particulates. As such, the large particulates and/or water droplets may flow passed the projection 262 without flowing through the opening 264 due to the momentum of the large particulates and/or water droplets reducing a likelihood of a change in direction. By doing this, smaller particulates may enter a hollow space of the second inner tube 240 and turn in a direction angled to arrow 298, while large particulates and/or water droplets are substantially prevented from entering the hollow space and flow substantially parallel to arrow 298.

Exhaust gas may enter an interior of the second inner tube 240 via the opening 264 located on the projection 262. The exhaust gas flows up toward the inset portion 252 before flowing out the perforations 268 directly toward the PM sensor element 254 in the annular space 270. The exhaust gas may deposit a portion of its particulate matter onto the sensor substrate 216 before flowing toward the bottom 212 of the first outer tube 250. The exhaust gas then flows through either the first outlet 280 or the second outlet 282 and enter the exhaust passage 48. The flow of exhaust gas into the PM sensor 162 is described in greater detail below.

Thus, a PM sensor may comprise a first outer tube partially housing a second inner tube. The tubes are concentric and differently sized such that a curved sensor substrate may be located in an annular space 270 formed between the two tubes. The sensor substrate comprises a pair of spatially separated electrodes on a first surface, where a resistance of the electrodes is unequal (e.g., the resistance of a first electrode is greater than the resistance of a second electrode). The sensor substrate may be configured to capture PM in exhaust gas received by the second inner tube via an opening located on a projection of the second inner tube. Exhaust gas in the second inner tube flows through a plurality of perforations facing the first surface of the sensor substrate into the annular space 270. The exhaust gas may deposit PM onto the substrate before flowing through an outlet of the first outer tube. As PM accumulates on the sensor substrate, the electrodes may bridge, thereby reducing an electrical resistance of the electrode with the greater electrical resistance to an electrical resistance substantially equal to the lower electrical resistance of the other electrode. A heating element coupled to a second surface of the sensor substrate may be activated to burn the accumulated PM in response to a measured increased current in response to the decreased electrical resistance. Additionally, one or more cylinder operating conditions may be altered to promote a regeneration of a particulate filter in an exhaust passage upstream of the PM sensor in response to the bridging of the electrodes. This may initiate regeneration of the particulate filter and the PM sensor.

Figure 3C:
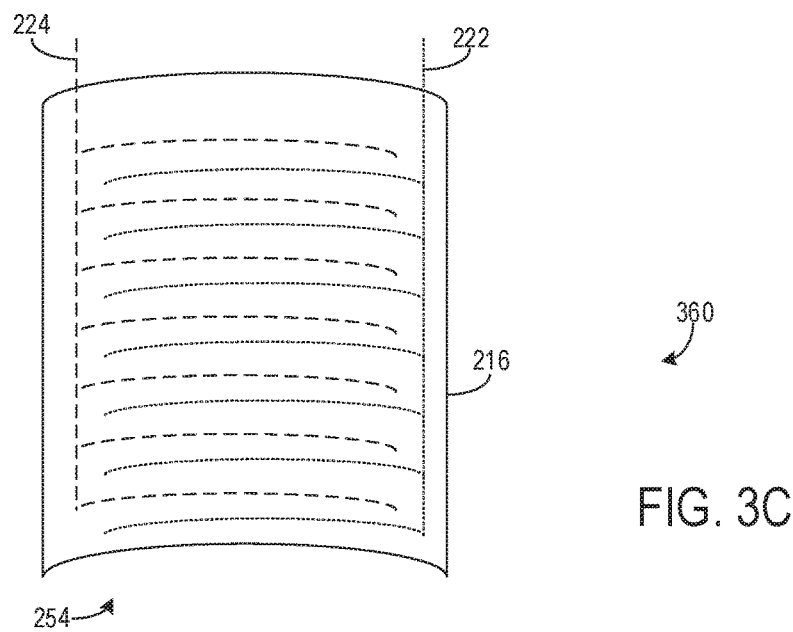
FIGS. 3C and 3D show detailed views of a first surface and a second surface of a PM sensor element in the PM sensor assembly.
Figure 3D:
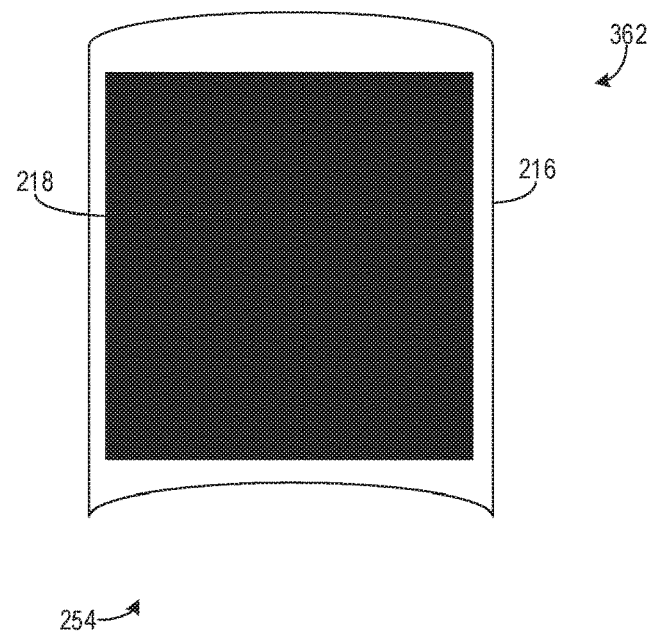

FIG. 3A shows an exterior side perspective view 300 of PM sensor 162. FIG. 3B shows a top-down view 325 of PM sensor 162. Portions of the PM sensor 162 in the exterior side perspective view 300 are transparent, exposing an interior of the PM sensor 162, including PM sensor element 254 and second inner tube 240. FIGS. 3C and 3D depict detailed illustrations of the PM sensor element 254.

Turning now to FIG. 3A, it shows an exterior view 300 with an example exhaust flow through the PM sensor 162. Exhaust gas from an engine (e.g., engine 10 shown in FIG. 1) is expelled into an exhaust passage (e.g., exhaust passage 48 shown in FIG. 1) to which the PM sensor 162 is coupled.

Exhaust gas in the exhaust passage is indicated via solid line arrows. Exhaust gas in the second inner tube 240 is indicated by small dash line arrow and exhaust gas in the annular space 270 between the first outer tube 250 and second inner tube 240 is indicated by large dash line arrows. Large dash lines are bigger (e.g., longer) than small dash lines.

Incoming exhaust flow 302 (also called incoming exhaust or incoming exhaust gas) refers to exhaust upstream of the PM sensor 162, which enters the opening 264 of the PM sensor. As such, the exhaust flow 302 is the exhaust gas that exits the PF (e.g., PF 72 shown in FIG. 1), for example. Furthermore, particulates delivered to the PM sensor 162 may have passed through the PF. The incoming exhaust flow 302 may flow through the exhaust passage without contacting or flowing into the PM sensor 162. A portion of incoming exhaust flow 302 gets blocked by upstream wall 208 of the first outer tube 250 and/or upstream face 242 along the bottom portion 260 of the second inner tube 240, and only a remaining portion of the incoming exhaust flow 302, indicated as exhaust flow 304 flows into the opening 264. As such, a remaining portion of exhaust gas flows downstream of the PM sensor 162 as shown by arrow 314 (herein referred to as downstream exhaust flow 314).

As the exhaust flow 304 deviates from the incoming exhaust flow 302, large particulates and/or water droplets (as shown by circles 320) may continue flowing in the horizontal direction passed the PM sensor 162 with incoming exhaust flow 302. Thus, the greater momentum of the large particulates and/or water droplets inhibits a turning and/or direction change of the large particulates and/or water droplets into the opening 264 of the projection 262.

The exhaust flow 304 flows into the projection 262 before flowing through the opening 264 and into the interior space of the first inner tube 240. The exhaust flow 304 flows up the second inner tube 240, against the direction of gravity 299, before flowing through the perforations 268 on the front face of the second inner tube 240. In one example, the perforations 268 are the only openings fluidly coupling an interior of the second inner tube 240 to the annular space 270. In this way, exhaust gas flow 304 in the second inner tube 240 may not mix with exhaust gas in the annular space 270 without flowing through the perforations 268.

Turning now to FIG. 3B, it shows a detailed illustration of exhaust gas flowing out of the second inner tube 240, via perforations 268, and into the annular space 270 between the first outer tube 250 and the second inner tube 240. Exhaust gas flow 304 exits the second inner tube 240 via the perforations 268 in a radially outward direction toward the electrodes 220 of the sensor substrate 216. Exhaust flow 304 collides with the sensor substrate 216, in which particulates in the sensor substrate 216 may be deposited onto a first surface 360 of the sensor substrate 216 comprising the electrodes 220. As shown, the first surface 360 of the sensor substrate 216 faces an exterior surface of the second inner tube 240 and a second surface 362 faces an interior surface of the first outer tube 250. The particulates may accumulate onto or between individual electrodes of the electrodes 220. The electrodes may be electrically coupled in response to oppositely charged electrodes becoming bridged due to the deposited soot. After colliding with the sensor substrate 216, the exhaust gas flow 304 may flow in a circular direction in the annular space 270. Exhaust gas in the annular space 270 may contact the heating element 218 on the second surface 362. However, exhaust gas entering the annular space 270 from the second inner tube 240 may not flow directly into the heating element without flowing around the sensor substrate 216, in some examples.

Specifically, as shown in FIG. 3C, the first surface 360 of the PM sensor element 254 comprises the pair of interdigitated electrodes 222 and 224. The electrodes 222 and 224 are fixed to the sensor substrate 216, which is configured to capture soot from exhaust gas flowing out of the perforations 268 of the second inner tube 240. The pair of electrodes 222 and 224 traverse a portion of the curvature of the sensor substrate 216 such that the electrodes 222 and 224 are located directly across from the perforations 268. Soot (e.g., particulate matter) may accumulate between the pair of interdigitated electrodes 222 and 224, where soot electrically couples (e.g., bridges) the electrodes 222 and 224 upon reaching a threshold soot load. FIG. 3D shows the second surface 362 of the PM sensor element 254 having the heating element 218 physically coupled to the sensor substrate 216. The second surface 262 is opposite the first surface 260 such that the heating element 218 faces an opposite direction that the pair of electrodes 222 and 224 face. Specifically, the first surface 260 faces the perforations 268 on an exterior surface of the second inner tube 240 while the second surface 262 faces an interior surface of the first outer tube 250.

Returning to FIG. 3A, exhaust gas flow 304 flows downward in the annular space 270. Specifically, the direction of exhaust gas flow 304 in the annular space 270 is substantially opposite to the direction of exhaust gas flow 304 in the second inner tube 240, despite both directions being parallel to the central axis 295 of the PM sensor 162. Exhaust gas flow 304 in the annular space 270 may mix with exhaust gas in the exhaust passage 48 after flowing through either the first outlet 280 or the second outlet (e.g., second outlet 282). Exhaust gas flowing out of the first 280 or second outlets initially flows in a direction perpendicular to the direction of incoming exhaust flow 302 before turning and flowing parallel to the incoming exhaust flow 302, as shown by arrow 306.

Thus, FIGS. 3A and 3B illustrate a PM sensor configured to receive a portion of exhaust through an inner tube partially housed within an outer tube. The exhaust gas flows through a projection of the inner tube adapted to limit or prevent large particulates and/or water droplets from entering the PM sensor. By doing this, small particulates may flow up the inner tube, through a plurality of perforations, and into a sensor substrate without depositing large particulates and/or water droplets. This may improve diagnostic measurements of a PF upstream of the PM sensor due to a more uniform particulate deposition onto the sensor substrate. Electrodes are coupled to a first surface of the sensor substrate directly across from the perforations in the annular space. As such, exhaust gas flowing through the perforations may flow directly toward the first surface of the sensor substrate before colliding with the sensor substrate and flowing through a remained of the annular space. The exhaust gas then flows downward through the annular space to the outlets located on the outer tube. Thus, the exhaust gas flows from the annular space, through the outlets, and into an exhaust passage, where the exhaust gas from the PM sensor merges with exhaust gas in the exhaust passage.

Turning now to FIG. 4, a method 400 is shown for determining if a particulate filter in an exhaust passage is degraded via comparing a regeneration time interval of a PM sensor to a threshold time interval. Instructions for carrying out method 400 may be executed by a controller (e.g., controller 12 shown in FIG. 1) based on instructions stored on a memory of the controller and in conjunction with signals received from various sensors of the engine system, such as the sensors described above with reference to FIGS. 1, 2, 3A, and 3B. The controller may employ engine actuators of the engine system to adjust engine operation, according to the methods described below.

At 402, the method 400 includes determining and/or estimating and/or measuring current engine operating parameters. The current engine operating parameters may include, but are not limited to, engine temperature, vehicle speed, engine load, manifold vacuum, EGR flow rate, throttle position, and air/fuel ratio.

At 404, the method 400 includes measuring an electrical resistance of one or more of the pair of electrodes coupled to the sensor element. As described above, one of the electrodes may have a higher resistance than the other electrode. The resistance of the electrode with the higher resistance may be reduced once the electrodes are electrically coupled by soot bridging the electrodes. In some examples, the resistances of the two electrodes are substantially equal in response to the electrodes being bridged.

At 406, the method 400 includes determining if the electrodes are coupled. This may be determined by a decreased electrical resistance indicated by an increase in the current measured by a measurement device for a fixed voltage source (e.g., the measurement device 226 and the fixed voltage source 228 shown in FIG. 2). If the electrical resistance has not decreased, then the method 400 proceeds to 408 to maintain current engine operations and does not regenerate the sensor element. The method 400 also maintains a switch of a circuit electrically coupled to the heating element to remain open. For example, a controller 12 signals to maintain switch 232 of voltage source 230, as shown in FIG. 2, open such that a regeneration of the sensor substrate 216 does not occur (e.g., the heating element 18 shown in FIG. 2 is not activated).

If the electrodes are coupled, then the method 400 proceeds to 410 to activate the heating element by closing the voltage source to regenerate the sensor element. For example, controller 12 signals to actuate switch 232 of circuit voltage source 230 to a closed position to allow heating element 218 to heat the sensor element. As described above, by heating the sensor element, a temperature of the sensor element may be high enough to burn off some or all of the soot accumulated onto the sensor substrate of the sensor element. This may de-couple the pair of electrodes.

The switch remains in the closed position until the regeneration is complete, in one example. A complete regeneration may include burning off substantially all of the soot stored on the sensor substrate of the sensor element. A partial regeneration may include burning off some of the soot stored on the sensor element. The complete regeneration may be longer than the partial regeneration. At 412, the method 400 includes terminating the regeneration. The regeneration may be terminated in response to the electrodes no longer being bridged, which is determined when the electrical resistances of the electrodes are again unequal, as indicated by a decrease in the current measured by a measurement device to a fixed voltage source. In some embodiments, additionally or alternatively, the regeneration may be terminated after a set duration of time (e.g., 20 seconds). The duration of time may be based on an average amount of regeneration time used return the sensor substrate to a relatively low soot load (e.g., electrodes are not bridged and soot load is substantially equal to zero).

In some examples, the electrodes no longer being bridged may indicate a partial regeneration of the sensor element, wherein some of the PM stored on the sensor substrate has been burned off. Thus, the regeneration may be terminated following a PM sensor soot load reaching a threshold regeneration soot load, where the threshold regeneration soot load is based on a soot load of the sensor substrate being relatively low (e.g., substantially equal to zero, as described above). This may defined as a complete regeneration. In some examples, the method may employ both partial and complete regenerations based on PM sensor regeneration conditions being met and/or engine conditions. In some embodiments, the sensor element may be completely regenerated following a key-off event where the engine is shutdown. As such, the controller may remain active for the duration of the regeneration before being deactivated following termination of the regeneration.

Additionally or alternatively, the method 400 may further initiate a regeneration of a particulate filter in the main exhaust passage (e.g., particulate filter 72 in exhaust passage 48) when the electrodes are bridged. In this way, the particulate filter and the sensor element may be simultaneously regenerated. Regenerating the particulate filter may include adjusting a combination of one or more engine conditions including delaying a fuel injection, increasing a fuel injection pressure, retarding spark, increasing an air/fuel ratio, etc. In some examples, by adjusting the engine operation in this way, the sensor element may also be regenerated without activating the heating element. Engine operation may return to a nominal engine operation (e.g., stoichiometric air/fuel ratio, desired fuel injection timing, desired fuel injection pressure, optimal spark timing, etc.) in response to a tip-in. Therefore, the regenerations of the particulate filter and the sensor element may be initiated and terminated at the same time. In other examples, the regeneration of the particulate filter may be carried out by a heating element coupled to the particulate filter. In one example, the regeneration of the particulate filter may be terminated in response to the regeneration of the sensor element being terminated. In another example, the regeneration of the particulate filter may be terminated in response to a pressure difference between directly upstream of the particulate filter and directly downstream of the particulate filter being less than a threshold difference. In this way, a backpressure upstream of the particulate filter is sufficiently reduced such that exhaust gas may flow through the filter at a desired flow rate. The regeneration of the sensor element may also be terminated in response to the pressure difference upstream and downstream of the PF being less than the threshold difference. In some examples, the sensor element and the particulate filter may be regenerated independent of each other.

At 414, the method 400 includes determining a time interval between a last regeneration and a current regeneration of the sensor element. The last regeneration is defined as a regeneration event that occurred directly before the current regeneration event. The time interval may be calculated based on a duration of time between initiation of the last regeneration and initiation of the current regeneration (e.g., 120 minutes). A time interval may be less than a previous time interval as the particulate filter in the main exhaust passage becomes degraded and captures less soot. For example, the particulate filter develops leaks due to high regeneration temperatures, road conditions, etc., which may allow a greater amount of soot to flow to the PM sensor, resulting in more frequent regenerations of the sensor element.

At 416, the method 400 determines if the measured time interval is less than a threshold time interval. The threshold time interval may be based on a set threshold (e.g., 200 minutes), a last time interval measured, or a percentage of the last time interval measured (e.g., 50% of the last time interval). Further, the threshold time interval may be based on a threshold that indicates that the time interval is decreasing and the sensor element is being regenerated at an increasing rate. Additionally or alternatively, the threshold time interval may be adjusted based on engine operating parameters. For example, the threshold time interval may decrease as an engine load increases. Other examples may include where the threshold time interval may increase if the PF and/or sensor substrate are passively regenerated due to engine operating parameters.

If the time interval is not less than the threshold time interval, then the method 400 proceeds to 408 to maintain current engine operation and does not flag the particulate filter as being degraded.

If the time interval is less than the threshold time interval, then the method 400 proceeds to 418 to indicate (e.g., flag)

the particulate filter of the main exhaust passage, upstream of the PM sensor, is degraded. Indication of the particulate filter being degraded may include adjusting an engine operation and activating an indicator lamp 420 (e.g., in order to indicate to a vehicle operator that the particulate filter is degraded and needs to be replaced).

As an example, a controller (e.g., controller 12) may signal various actuators of an engine (e.g., throttle 62 of engine 10) to limit a torque output of the engine to reduce exhaust produced to meet emissions standards. As another example, additionally or alternatively, the method 400 may advance one or more of a spark timing and fuel injection, increase air/fuel ratio, and/or increase EGR. By increasing EGR flow to one or more cylinders of the engine, a combustion mixture temperature(s) is decreased and a volume of fuel injection may be decreased. By doing this, an amount of soot being exhausted from one or more cylinders of the engine may be decreased.

Thus, the method of FIG. 4 provides for a method comprising during a first condition when sensor element regeneration conditions are met and in response to the time interval being greater than a threshold time interval, regenerating the particulate filter in the engine exhaust pipe via a combination of one or more of retarding spark and decreasing an air/fuel ratio while regenerating the sensor element via a heating element. During a second condition and in response to the time interval being less than the threshold time interval, indicating to an operator degradation of the particulate filter and adjusting an engine actuator to reduce torque output.

Turning now to FIG. 5, it shows an operating sequence 500 illustrating example results for an engine comprising a PM sensor downstream of a PF (e.g., such as PM sensor 162 downstream of PF 72 shown in the embodiment of FIG. 1). The first plot 502 of 500 shows if the PM sensor element of the PM sensor is regenerating (e.g., the heater is activated). The second plot 504 shows if the PF in the exhaust passage upstream of the PM sensor is degraded. The third plot 506 shows the PM sensor element PM load. Dashed line 508 depicts a threshold PM load and dashed line 510 depicts a threshold regeneration PM (soot) load. Double headed arrows I1, I2, and I3 represent measured time intervals between a last regeneration and a current regeneration of the sensor element. The horizontal axes of each plot represent time and time increases from the left side of the figure to the right side of the figure.

FIG. 5 is illustrative by nature and time intervals between regenerations of the PM sensor element may be greater than or less than the time intervals depicted. Additionally or alternatively, degradation of the particulate filter in the main exhaust passage may occur over a threshold mileage (e.g., 25,000 miles).

Prior to t1, the PM sensor element is relatively clean due to PM sensor element load being less than the threshold PM load (plot 506 and line 508 respectively). The PM sensor element load is increasing from a load substantially equal to the threshold regeneration PM load (line 510), indicating that the PM sensor element has recently regenerated. Since the PM sensor element load is less than threshold PM load (line 508), a regeneration (line 502) is not occurring. Furthermore, enough regenerations have not occurred to be able to compare time intervals between two regenerations against a threshold time interval. As such, the PF is not degraded, as shown by line 504.

At t1, the PM sensor element load reaches the threshold PM load. Thus, the electrodes of the PM sensor element may be bridged due to accumulated soot on a first surface of the PM sensor element. As such, a regeneration of the PM sensor element is initiated by activating a heating element coupled to a second surface of the PM sensor element. The heating element may heat a sensor substrate of the PM sensor element, which may burn off some particulate matter stored on the surfaces of the PM sensor element. A regeneration of a PF in the exhaust passage upstream of the PM sensor may also be activated. The PF is not determined to be degraded.

After t1 and prior to t2, the PM sensor element load decreases below the threshold PM load toward the threshold regeneration PM load. The regeneration remains active (e.g., the heating element is still in an on position). In some examples, the regeneration may be terminated following the PM sensor element load decreasing below the threshold PM load. As such, the regeneration may be a partial regeneration. Additionally, the threshold time interval measured between regenerations of the PM sensor element may be adjusted following the partial regeneration. Specifically, the threshold time interval is decreased following the partial regeneration of the PM sensor element. In this way, the threshold time interval following a complete regeneration (e.g., a regeneration terminated following the PM sensor element soot load decreasing below the threshold regeneration PM load) may be equal to a greater amount of time compared to the threshold time interval following a partial regeneration. The PF is not determined to be degraded.

At t2, the PM sensor element is relatively clean, indicated by the PM sensor element load being equal to the threshold regeneration PM load. Thus, the regeneration is terminated (e.g., the heating element is deactivated). As such, the threshold regeneration PM load may represent a PM load following a complete regeneration of the PM sensor element. The PF is not determined to be degraded. Between t2 and t3, the PM sensor element load increases passed the threshold regeneration PM load toward the threshold PM load. The PF is not degraded.

At t3, the PM sensor element load exceeds the threshold soot load and in response, the regeneration is initiated. During the course of the metal filter regeneration, the time interval between the start of the current regeneration and the start of the last regeneration is measured, as shown by I1. I1 measures a time interval between t1 and t3. If the time interval is less than a threshold time interval then the particulate filter of the exhaust passage may be degraded, as described above. In this example, I1 is greater than the threshold time interval (e.g., two thirds of a previous regeneration) and the particulate filter in the exhaust passage is not degraded. The time interval in the example of the figure is depicted as a threshold amount of time. As described above, the time interval may vary based on engine conditions or may be based on previous time intervals between subsequent regenerations.

Between t3 and t4, the regeneration of the PM sensor element continues. As a result, the PM sensor element load decreases below the threshold PM load toward the threshold regeneration PM load. The PF is not degraded. At t4, the PM sensor element has been completely regenerated as indicated by the PM sensor element load being substantially equal to the threshold regeneration PM load. The regeneration is terminated. The PF is not degraded.

After t4 and before t5, the PM sensor element load begins to increase from the threshold regeneration PM load to the threshold regeneration load following termination of the regeneration of the PM sensor. The regeneration is still disabled and the PF is not degraded.

At t5, the PM sensor element load exceeds the threshold PM load. In response, regeneration of the PM sensor element is initiated. I2 is measured similar to the measurement of I1, except it measures a time interval between t5 and t3. I2 is greater than the threshold time interval and the particulate filter in the exhaust passage is not degraded. Between t5 and t6, the regeneration continues and as a result, the PM on the PM sensor element is burned off. Thus, the PM sensor element load decreases below the threshold PM load toward the threshold regeneration PM load. The PF is not degraded.

At t6, the PM sensor element load is substantially equal to the threshold regeneration PM load. In response, the regeneration is terminated. The PF in the exhaust passage is not degraded.

After t6 and prior to t7, the PM sensor element load increases toward the threshold PM load. As shown, the rate of PM sensor element load increase between t6 and t7 is greater than the rates of increase between both t4 and t5 and t2 and t3. This may indicate a greater amount of PM flowing through the PF in the exhaust passage.

At t7, the PM sensor element load is greater than or equal to the threshold PM load. Thus, the regeneration is initiated. I3 measures a time interval between t7 and t5. I3 is less than the threshold time interval and thus, the PF in the exhaust passage is degraded, as depicted by line 504. A controller (e.g., controller 12) may indicate degradation of the PF disposed upstream of PM sensor in the exhaust passage in response to the time interval decreasing below the threshold time interval. Furthermore, the controller may adjust engine operation in response to the degraded particulate filter. The adjustments may include one or more of turning on an indicator lamp and limiting a vehicle torque output, as described above with respect to FIG. 4.

Thus, during a first condition where the electrodes are bridged and the time interval is not less than a threshold time interval, the PM sensor element is regenerated without indicating the PF being degraded. During a second condition where the electrodes are bridged and the time interval is less than the threshold time interval, the PM sensor element is regenerated and the PF is flagged as being degraded, which may further include adjusting engine operations to accommodate the degradation to the PF. In some example, the adjusting may be more extreme (e.g., greater reduction in torque) based on a difference between a measured time interval and the threshold time interval. That is to say, a time interval much less than the threshold time interval may lead to a greater reduction in torque than a time interval slightly less than the threshold time interval.

After t7 and prior to t8, the regeneration of the PM sensor element continues. As the regeneration takes place, the PM sensor element load decreases toward the threshold regeneration PM load. The PF in the exhaust passage remains degraded.

At t8, the regeneration of the PM sensor element is terminated via actuating the switch of the electric circuit to an open position in response to the PM sensor element load decreasing below the threshold regeneration PM load, as described above. The PF in the exhaust passage remains degraded.

After t8, the adjustments are maintained. The regeneration is disabled and the PM sensor element load is substantially equal to the threshold regeneration PM load. The particulate filter in the exhaust conduit remains degraded.

In this way, a particulate matter sensor located downstream of a particulate filter in an exhaust passage may be used to determine a degradation of the particulate filter. The particulate matter sensor may include first outer tube with a second inner tube located interior to the first outer tube. The second inner tube is configured to receive a portion of exhaust gas downstream of the particulate filter via a concave projection protruding into an interior space of the second inner tube. The second inner tube further comprises a plurality of perforations for expelling exhaust gas from the second inner tube to an annular space located between the tubes. A PM sensor element configured to capture particulate matter from the exhaust gas expelled from the second inner tube is located in the annular space directly across from the perforations with a pair of electrodes facing the perforations. As the PM accumulates onto the electrodes, the electrodes may bridge and indicate a regeneration demand of either the PM sensor or the particulate filter. Furthermore, a time interval between subsequent regenerations may be measured. The technical effect of measuring a time interval between subsequent regenerations is to determine a degradation of the particulate filter. An increased amount of particulate matter may flow through the particulate filter to the particulate matter sensor due to cracks and/or holes forming in the particulate filter. As a result, the time interval between subsequent regenerations may decrease below a threshold time interval as the particulate filter is degraded. By doing this, the particulate matter sensor may indicate one or more of a regeneration demand and a degradation of the particulate filter in the exhaust passage.

A system for an engine includes a particulate matter sensor disposed along an exhaust passage comprising an outer tube coaxial with an inner tube having a concave bottom with a central opening, and where perforations of the inner tube face a curved sensor element located in an annular space between the outer tube and the inner tube. A first example of the system further includes where the inner tube is partially housed within the outer tube, and where the inner tube is radially spaced away from the outer tube, and wherein the sensor element is formed on a curved substrate surface positioned in a gap between the outer tube and inner tube. A second example of the system optionally including the first example further includes where the sensor element comprises an electrical surface on a first surface facing the perforations of the inner tube, the sensor element further comprises a heating element on a second surface facing an interior surface of the outer tube. A third example of the system optionally including the second and/or first examples further includes where each of the outer tube and the inner tube is sealed at its top with respect to vertical when coupled in the exhaust passage of a vehicle traveling on a road. A fourth example of the system optionally including one or more of the first through third examples further includes where the outer tube has a sealed bottom physically coupled to the inner tube, and where a lower portion of the inner tube extends vertically below the sealed bottom into the exhaust passage. A fifth example of the system optionally including one or more of the first through fourth examples further includes where the concave bottom is a bell-shaped projection extending toward an interior space of the inner tube, and where the central opening is located on a plane of the projection co-planar with a bottom of the outer tube. A sixth example of the system optionally including one or more of the first through fifth examples further includes where the outer tube comprises two outlets including a first outlet on a front face and a second outlet on a back face, and where the first and second outlets are directly across from each other. A seventh example of the system optionally including one or more of the first through sixth examples further includes where upstream surfaces the inner tube and the outer tube are normal to and face a flow of incoming exhaust gas in the exhaust passage. An eighth example of the system optionally including one or more of the first through seventh examples further includes where the outer tube and the inner tube are hollow and concentric with each other.

A method for an engine includes adjusting engine operation based on degradation of a particulate filter in an engine exhaust pipe, the degradation determined based on a time interval between a first regeneration and a second regeneration of a curved particulate matter sensor element located in an annular space between concentric, hollow inner and outer tubes. A first example of the method further includes where an inlet of the inner tube fluidly coupled to the exhaust passage located on a curved projection projecting into an interior space of the inner tube, a plurality of perforations of the inner tube located on a front surface of the inner tube facing a pair of interdigitated electrodes on a first surface of the particulate matter sensor element. A second example of the method optionally including the first example further includes where the particulate matter sensor element is spaced away from the inner tube and the outer tube and configured to capture particulate matter in the exhaust gas flowing through the perforations. A third example of the method optionally including the first and/or second examples further includes where regenerating the particulate matter sensor element in response to a variation in an electrical resistance of a pair of electrodes, where the electrical resistance decreases in response to the pair of electrodes being electrically coupled. A fourth example of the method optionally including one or more of the first through third examples further includes where during a first condition when particulate filter regeneration conditions are met and in response to the time interval being greater than a threshold time interval, regenerating the particulate filter in the engine exhaust pipe via a combination of one or more of retarding spark and decreasing an air/fuel ratio, and during a second condition and in response to the time interval being less than the threshold time interval, indicating to an operator degradation of the particulate filter and adjusting an engine actuator to reduce torque output.

An engine exhaust system includes an exhaust passage comprising a particulate matter sensor comprising inner and outer hollow cylindrical tubes with an annular space located therebetween, the sensor further comprising a sensor substrate located in the annular space with a first surface comprising interdigitated electrodes facing a plurality of perforations on an exterior surface of the inner tube. The engine exhaust system further comprising a controller with computer readable instructions for determining when the pair of electrodes are coupled, activating a regeneration of the sensor substrate in response to the electrodes being coupled, and indicating a degradation of a particulate filter upstream of the particulate matter sensor in the exhaust passage when a time interval between subsequent regenerations is less than a threshold time interval. A first example of the engine exhaust system further includes where exhaust gas enters the particulate matter sensor via an opening located on a bell-shaped projection of the inner tube and where exhaust gas exits the particulate matter sensor via a pair of outlets located on the outer tube. A second example of the engine exhaust system optionally including the first example further includes where the opening is coplanar with and vertically equal to a sealed bottom of the outer tube physically coupled to an exterior surface of the inner tube. A third example of the engine exhaust system optionally including the first and/or second examples further includes the sensor substrate is configured to capture particulate matter and where a second surface of the sensor substrate comprises a heating element regenerating the sensor substrate. A fourth example of the engine exhaust system optionally including one or more of the first through third examples further includes where the inner and outer tubes share a central axis and where the tubes are sealed at a top physically coupled to an exhaust pipe. A fifth example of the engine exhaust system optionally including one or more of the first through fourth examples further includes where the sensor substrate traverses a portion of the circumference of the inner tube.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:
1. An engine exhaust system comprising:
an exhaust passage comprising a particulate matter sensor comprising inner and outer hollow cylindrical tubes with an annular space located therebetween, the particulate matter sensor further comprising a sensor sub- strate located in the annular space with a first surface comprising a pair of interdigitated electrodes facing a plurality of perforations on an exterior surface of the inner tube; and a controller with non-transitory computer readable instructions for determining when the pair of interdigitated electrodes is coupled, activating a regeneration of the sensor substrate in response to the pair of interdigitated electrodes being coupled, and indicating a degradation of a particulate filter upstream of the particulate matter sensor in the exhaust passage when a time interval between subsequent regenerations is less than a threshold time interval.

2. The engine exhaust system of claim 1, wherein exhaust gas enters the particulate matter sensor via an opening located on a bell-shaped projection of the inner tube, and where exhaust gas exits the particulate matter sensor via a pair of outlets located on the outer tube.

3. The engine exhaust system of claim 2, wherein the opening is coplanar with and vertically equal to a sealed bottom of the outer tube physically coupled to the exterior surface of the inner tube.

4. The engine exhaust system of claim 1, wherein the sensor substrate is configured to capture particulate matter, and further comprising a second surface of the sensor substrate that includes a heating element for regenerating the sensor substrate.

5. The engine exhaust system of claim 1, wherein the inner and outer tubes share a central axis and are sealed at a top physically coupled to an exhaust pipe.

6. The engine exhaust system of claim 1, wherein the sensor substrate traverses a portion of a circumference of the inner tube.

* * * * *